United States Patent
Conrads et al.

(10) Patent No.: US 7,134,350 B2
(45) Date of Patent: Nov. 14, 2006

(54) METHOD AND APPARATUS FOR PRODUCING SAMPLES OF PRIMARILY FINELY GRANULATED AND DRY MATERIAL

(75) Inventors: Hans Georg Conrads, Hannover (DE); Volkhard Klupsch, Barleben (DE); Thomas Hoepfel, Halle (DE)

(73) Assignee: Promecon Prozess- und Messtechnik Conrads GmbH., Barleben (DE)

( * ) Notice: Subject to any disclaimer, the term of this patent is extended or adjusted under 35 U.S.C. 154(b) by 0 days.

(21) Appl. No.: 10/068,577

(22) Filed: Feb. 5, 2002

(65) Prior Publication Data
US 2002/0105341 A1    Aug. 8, 2002

(30) Foreign Application Priority Data
Feb. 5, 2001    (DE) .................... 101 05 117

(51) Int. Cl.
*G01N 1/20* (2006.01)
(52) U.S. Cl. .................... 73/863.91; 73/863.43
(58) Field of Classification Search ............. 73/863.43, 73/865.8, 866
See application file for complete search history.

(56) References Cited
U.S. PATENT DOCUMENTS
4,091,967 A * 5/1978 Kinoshita .................... 222/238
4,498,338 A * 2/1985 Peltonen et al. ............ 73/865.8
5,173,662 A   12/1992 Trerice et al.
5,639,202 A * 6/1997 Roycraft ..................... 414/412

FOREIGN PATENT DOCUMENTS
| DE | 33 03 117 | 8/1983 |
| DE | 34 16 821 | 11/1985 |
| DE | 251 623 | 7/1986 |
| DE | 42 24 128 | 2/1994 |
| DE | 198 56 870 | 6/1999 |

* cited by examiner

Primary Examiner—Daniel S. Larkin
Assistant Examiner—John Fitzgerald
(74) Attorney, Agent, or Firm—Karl Hormann

(57) ABSTRACT

An apparatus and a method for producing samples of a finely granular and dry material for measuring the residual carbon content thereof. The material is fed by a torque monitored conveyor screw to a measuring chamber and is progressively compacted therein. At an abrupt increase in screw torque feeding of the material ceases yielding a sample in the measuring chamber of a reproducible degree of compaction.

6 Claims, 1 Drawing Sheet

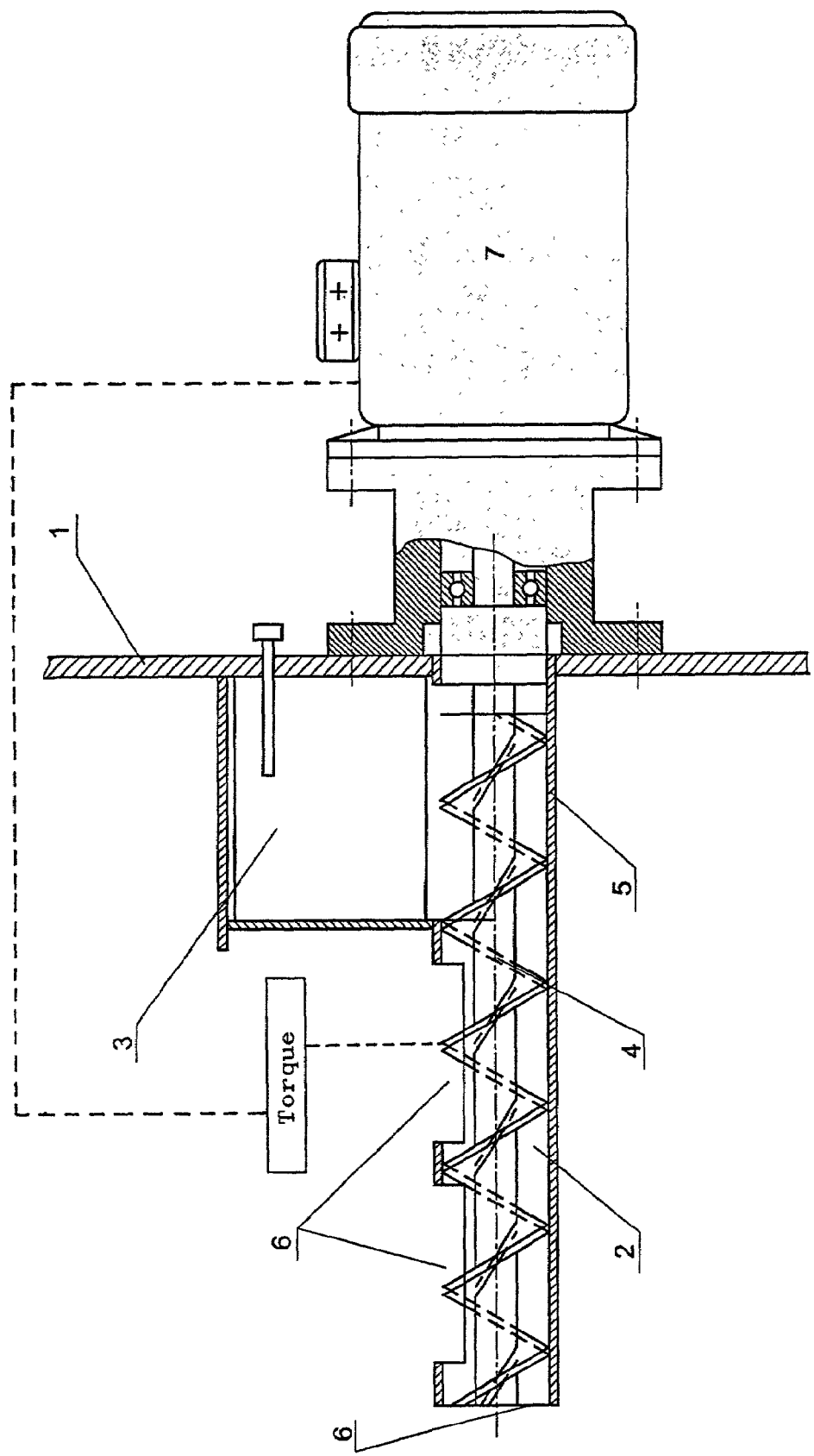

METHOD AND APPARATUS FOR PRODUCING SAMPLES OF PRIMARILY FINELY GRANULATED AND DRY MATERIAL

BACKGROUND OF THE INVENTION.

1. Field of the Invention

The invention, in general relates to a novel method and apparatus for producing samples of primarily finely granulated and dry material and, more particularly, to a method and apparatus for producing samples of pulverized combustion residue such as, for example, filter and fly ash, for defining their residual carbon content by defining changes in electrical parameters of a complex electrical component which includes the produced samples of primarily finely granulated and dry material to be examined.

The invention is intended especially for use in ash collection sites of furnaces in coal-fired power plants. In this connection, reference is made primarily to fly ash without, however, intending thus to limit the field of application of the invention. For the invention is advantageously applicable wherever residual carbon contents of mainly finely granulated and dry material is to be defined by defining changes in electrical parameters of complex electrical components which contain the material to be examined. In addition to furnaces of power plants this may also be incinerators and cement making plants.

Defining residual carbon contents of fly ash is necessary, on the one hand, for controlling and optimizing the combustion process, i.e., for use of as much of the energy as is contained in the fuel. On the other hand, defining residual carbon content is necessary for controlling the quality of fly ash to be used as an additive in building materials and cement. Under both aspects, the invention aims at providing as low a residual carbon content, or as low a proportion of uncombusted components, as possible. Changing load conditions in a firing plant and different fuel compounds require constant monitoring of the combustion process which, in turn, leads to the requirement of continuously defining the residual carbon content or periodically to define it in short intervals of time or with no or very little time lag.

2. Statement of the Prior Art

At present, the method employed by power plants is to draw samples followed by an analytic examination of the samples in a laboratory. This is expensive and results in such significant losses of time that for all intents and purposes it is impossible to optimize the combustion process.

For that reason efforts have not been wanting to develop methods and apparatus which make it possible to define residual carbon content in a simple manner, continuously or periodically, without any loss of time. In this connection, those methods have been found to be particularly suitable which are based upon a change in the electrical parameters of complex electric components which contain the fly ash to be measured. However, the handling of fly ash is extremely difficult because of its extremely complicated bulk behavior.

German Laid-Open Patent Specification No. DE-OS 33 03 177 disclosed a method and an apparatus for measuring the carbon content of fly ash in which the capacity of a capacitor is evaluated into which a sample of fly ash is introduced as a dielectric substance. Fly ash is removed from a silo by means of a feed screw and is transmitted to a measuring chamber which constitutes the nonconductor of the capacitor, and is compacted by vibration. Thereafter, the capacity of the measuring chamber containing the compacted fly ash is defined. After defining the capacity the fly ash is removed from the measuring chamber and returned to the silo by a different feed screw. The carbon content of the fly ash is deduced from the measured capacity. The method may be practiced continually or periodically, but in order to obtain useful measuring values care has to be taken in ensuring that the mean quantity of fly ash contained in the measuring chamber is substantially constant and of defined density.

A basically comparable solution has been described in German laid-open patent application No. 198 56 870. In this case, ash transported by a pneumatic feed system is fed to a sampler, care being taken to realize a predetermined particle content of the probe by way of exhaust filters and light barrier. The sample is heated to a predetermined analyzing temperature and is compacted by a shaking device. Thereafter it is subjected to a microwave analyzer. Microwave resonance techniques are used as is well known to define the residual carbon content of the prepared sample fed to the microwave analyzer. Once it has been examined, the sample is returned to the feed system.

Either method require rather complex apparatus for the withdrawal, preparation and return of the sample. The complexity is last not least owing to the extremely poor bulk behavior of the fly ash to be tested. Moreover, the attained precision of the residual carbon content has been found to be unsatisfactory. More particularly, the attained measuring values tend to be vastly scattered. Accordingly, they can only be conditionally used for controlling combustion processes.

OBJECTS OF THE INVENTION

It is an object of the invention to provide a method and an apparatus for producing samples of substantially finely granulated and dry materials.

A more particular object resides in the provision of a method and an apparatus for producing a sample of fly ash for determining its residual carbon content by defining changes in electrical parameters of a complex electrical component in which the sample to be examined is contained.

It is a further object of the invention to provide a method and apparatus of the kind referred to which is of comparatively insignificant complexity.

A still further object of the invention is to provide a simple method and an apparatus for furnishing measuring results of high accuracy.

SUMMARY OF THE INVENTION

These and other objects of the invention are accomplished by apparatus of the kind to be described. It is provided with a feed screw and a measuring chamber connected therewith. The measuring chamber is a complex electrical component into which fly ash is fed and compacted by the conveyor screw. Compaction of the chiefly finely granulated and dry material, i.e. fly ash, continues until the occurrence of an abrupt increase in the compaction force.

The hitherto practiced method of vibratory compaction of fly ash has been found not to yield reproducible results. Rather, in consequence of the vibration the fly ash remains in a fluidized condition. Moreover, the vibration has been found to result in demixing or segregation of the different components of the fly ash. In the known methods and apparatus for producing samples of fly ash to measure their residual carbon content, the non-reproducible compaction results as well as, in particular, the apparent segregation lead to vastly scattered measuring results. The results have been found to deviate by significantly more than ±0.5 percent.

The method in accordance with the invention is based upon the recognition that during compaction of fly ash, that once a reproducible degree of compaction has been reached, there occurs an abrupt increase of the compaction force of more than 200% without, however, yielding any increased degree of compaction. By evaluating this large and significant leap in the compaction force, compaction results may thus be attained in a simple manner which, by the measuring to be described, yield results of high accuracy and low scattering.

Placing the closed measuring chamber or complex electrical component and the feed screw into a container for receiving fly ash such that the feed screw conveys fly ash into the measuring chamber and compacts it until an abrupt increase in its torque occurs, has been found to be of particular advantage. By placing the complex electrical component in the fly ash receiving container, the temperature of the fly ash stays at the level of between about 60° C. and 90° C. normal in fly ash collection containers. Unlike the prior art methods and devices, this avoids the need for special means for heating the fly ash samples. The fly ash enters the measuring chamber over a short path and, after the measurement has been taken, the ash can be returned to the collection container by reversing the rotations of the feed screw. Advantageously, the screw conveyor is provided with an upwardly open catch trough for catching fly ash newly entering the container. A catching device of this kind should especially be provided if the screw conveyor is mounted in the collection container such that it is not always present in the pouring path of the fly ash.

Of course, the invention allows for the possibility of providing means for removing samples from the measuring chamber for external calibrating tests.

Aside from the precise results and insignificant scattering thereof achievable by practicing the method and utilizing the apparatus of the invention, its simplicity is considered to be of particular advantage. The apparatus consisting of the screw conveyor and complex electrical component measuring chamber as well as the method in accordance with the invention offer technical solutions which may be mastered without any problems and can be advantageously applied in many measuring situations for defining the residual carbon content of fly ash be defining the change of electrical parameters of a complex electrical component in which the samples of fly ash are received.

DESCRIPTION OF THE DRAWING

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of preferred embodiments when read in connection with the appended single drawing, which is a side elevation in partial section of an apparatus for practicing the invention.

DETAILED DESCRIPTION OF THE PREFERRED EMBODIMENT

Fly ash is collected in a container one side wall 1 of which is shown in the drawing. The apparatus in accordance with the invention consists of a screw conveyor 2 and of a complex electrical component 3 constituted as an enclosed measuring chamber. A feed screw 4 of the screw conveyor 2 rotates within a tube 5 which is provided with openings 6 at its front end as well as in its upper section. The openings 6 are adapted to take in as well as to discharge of fly ash. In the embodiment shown, the length and diameter of the screw conveyor are about 300 mm and about 40 mm, respectively. The upward openings 6 are about 60 mm long and extend around the circumference of the tube by about 40°. The feed screw 4 may be reversible driven by an electric motor 7 disposed at the exterior of the collection chamber. The complex electrical component 3 is mounted above the screw conveyor 2 and engages the side wall 1 of the collection container, the arrangement being such that fly ash may be conveyed by the feed screw 4 from the collection container into the measuring chamber 3, and vice versa by simple reversal of the rotations of the screw 4.

For taking samples, the apparatus is mounted on the side wall 1 of the collection container such that the screw conveyor 2 and the measuring chamber 3 are disposed within the collection chamber, preferably at a location which places them into the flow path of fly ash into the container. Fly ash enters the tube 5 of screw conveyor through its upper and front openings 6 whence it is fed to the measuring chamber of the complex electrical component 3 by rotating the screw 4 in the appropriate direction. While being fed into the measuring chamber 3, the fly ash is increasingly compacted therein. As soon as the torque of the feed screw 4 abruptly increases from about 0.1 Newtonmeter to about 0.3 Newtonmeter, the fly ash within the complex electric component 3 has reached a defined degree of compaction for defining the residual carbon content of the fly ash with sufficient accuracy by determining the change in the electrical parameters of the compact electric component 3. In the embodiment described the scattering of the measuring values or results is less than ±0.2 percent.

Following the measurement, the complex electrical component 3 is evacuated, and the fly ash is returned to the collection container, by reversing the rotation of the feed screw 4.

It will be understood by those skilled in the art that for determining the torque of the feed screw 4 at any giving moment it is monitored by a conventional gage (schemically shown) which may be provided with switches responsive to the torque for terminating rotation of the screw 4.

What is claimed is:

1. An apparatus for producing a sample of a mainly finely grained and dry material for defining the residual carbon content thereof as a function of a change in at least one electrical parameter, comprising:
   a measuring chamber;
   a screw conveyor connected to the measuring chamber and comprising a rotatable feed screw;
   means for rotating the feed screw at a predetermined torque for feeding the material to the measuring chamber for compaction therein; and
   means responsive to an abrupt increase in the torque for stopping rotation of the feed screw.

2. The apparatus of claim 1, wherein the measuring chamber and the screw conveyor are positioned in a chamber for collecting the material.

3. The apparatus of claim 1, wherein the screw conveyor comprises a tubular member for rotatably receiving the feed screw and provided with at least one opening for receiving the material.

4. A method of producing samples of a mainly finely granulated and dry material for determining the residual carbon content of the material, comprising the steps of:
   feeding the material at a predetermined force to a measuring chamber for compaction therein;
   monitoring the force; and
   interrupting the feeding of material at an abrupt increase in the force.

5. The method of claim 4, wherein the material is fed to the measuring chamber by a rotating conveyor screw and wherein the force is monitored as a function of the torque of the conveyor screw.

6. The method of claim 5, wherein feeding of the material is interrupted at an increase in torque by more than 200 percent.

* * * * *